United States Patent
Kuhne

(10) Patent No.: US 9,421,279 B2
(45) Date of Patent: *Aug. 23, 2016

(54) PROCESS FOR PREPARING PURIFIED NUCLEIC ACID AND THE USE THEREOF

(71) Applicant: Roche Diagnostics GmbH, Mannheim (DE)

(72) Inventor: Wolfgang Kuhne, Penzberg (DE)

(73) Assignee: Roche Diagnostics GmbH, Mannheim (DE)

( * ) Notice: Subject to any disclaimer, the term of this patent is extended or adjusted under 35 U.S.C. 154(b) by 51 days.

This patent is subject to a terminal disclaimer.

(21) Appl. No.: 14/277,415

(22) Filed: May 14, 2014

(65) Prior Publication Data

US 2014/0287026 A1 Sep. 25, 2014

Related U.S. Application Data

(60) Continuation of application No. 13/938,398, filed on Jul. 10, 2013, now abandoned, which is a division of application No. 13/545,427, filed on Jul. 10, 2012, now abandoned, which is a division of application No. 13/197,225, filed on Aug. 3, 2011, now abandoned, which is a division of application No. 12/627,449, filed on Nov. 30, 2009, now abandoned, which is a division of application No. 11/389,167, filed on Mar. 27, 2006, now abandoned, which is a division of application No. 10/771,371, filed on Feb. 5, 2004, now abandoned, which is a division of application No. 09/117,537, filed as application No. PCT/EP97/00321 on Jan. 24, 1997, now Pat. No. 6,750,333.

(30) Foreign Application Priority Data

Feb. 6, 1996 (EP) ..................... 96101628

(51) Int. Cl.
*C12N 15/10* (2006.01)
*A61K 48/00* (2006.01)
*C12N 15/85* (2006.01)

(52) U.S. Cl.
CPC ......... *A61K 48/005* (2013.01); *A61K 48/0091* (2013.01); *C12N 15/101* (2013.01); *C12N 15/85* (2013.01)

(58) Field of Classification Search
None
See application file for complete search history.

(56) References Cited

U.S. PATENT DOCUMENTS 5,990,301 A 11/1999 Colpan et al.
6,214,586 B1 4/2001 McNeilly
6,759,394 B2 7/2004 DeBenedetti et al.

FOREIGN PATENT DOCUMENTS

| EP | 0 268 946 B1 | 6/1988 |
|---|---|---|
| EP | 0 325 032 | 7/1989 |
| WO | WO 95/21177 | 8/1995 |
| WO | WO 95/21179 | 8/1995 |
| WO | WO 95/21250 | 8/1995 |
| WO | WO 96/02658 | 2/1996 |
| WO | WO 96/21729 | 7/1996 |

OTHER PUBLICATIONS

Declaration of Dr. Wolfgagn Kuhne dated May 9, 2014, 5 pages.
Clutterbuck et al., "Separation & Purification: Endotoxin Reduction Using Disposable Membrane Adsorption Technology in cGMP Manufacturing", BioPharm International, 2007, 20(5), 5 pages.
Qiagen Plasmid Purification Handbook, 1999, pp. 64-66.
Qiagen EndoFree Plasmid Purification Handbook, Appendix B: Removal of Bacterial Endotoxins, 2012, pp. 36-39.
Cotton et al., Gene Therapy 1 (1994) 239-246, "Lipopolysaccharide is a frequent contaminate of plasmid DNA preparations and can be toxic to primary human cells in the presence . . . ".
Johnson et al., Analyt. Biochem 132 (1983) 20-25, "Large-Scale Isolation of Plasmid DNA and Purification of λ Phage DNA using Hydroxylapatite Chromatography".
Horn et al., Human Gene Ther. 6 (1995) 565-573, "Cancer Gene Therapy Using Plasmid DNA: Purification of DNA for Human Clinical Trials".
Udvardy et al, Acta Biochim. et Biophys. Acad. Sci. Hung. 14 (1979) 141-146, "Simple Method for the Purification of Bacterial Plasmids on Hydroxyapatite".
Cliff et al., Artif. Cells Blood Substit. Immobil. Biotechnol. 23 (1995) 331-336, "A Comparative Study of the Accurate measurement of Endotoxin in Liposome-Encapsulated Hemoglobin".
Berzofsky, Altex. 12 (2) (1995) 93-97—PubMed Abstract, "Endotoxin Detection in Pharmaceuticals and Medical Devices with Kinetic-QCL, a Kinetic-Quantitative . . . ".
Liu et al., Clin. Biochem. 30 (1997) 455-463, "Removal of Endotoxin from Recombinant Protein Preparations".
McDonald et al., Protein Expression and Purification 8 (1996) 97-108, "Large-Scale Purification and Characterization of Recombinant Fibroblast Growth Factor-Saporin . . . ".
British Pharmacopeia (1998), vol. II, Appendix XIV C A212:Method A, 5 pages.

(Continued)

*Primary Examiner* — Jim Ketter

(74) *Attorney, Agent, or Firm* — Rothwell, Figg, Ernst & Manbeck, P.C.

(57) ABSTRACT

The invention relates to a nucleic acid preparation with a content of below 1% protein, preferably below 0.1% protein, free of ethidium bromide, phenol, cesium chloride and detergents based on octyl phenol poly(ethylene glycol ether)$_n$ and with a content of below 1 EU/mg DNA of endotoxins. Said preparation is suitable as a drug particularly in gene therapy.

1 Claim, No Drawings

(56) References Cited

OTHER PUBLICATIONS

Coleman et al, Eur. J. Biochem. 91 (1978) 303-310, "Rapid Purification of Plasmid DNAs by Hydroxyapatite Chromatography".
Bachvarov et al., Preparative Biochem. 13 (1983) 161-166, "Large Scale Purification of Plasmid DNA".
Pakroppa et al., Analytical Biochem. 67 (1975) 372-383, "Isolation of Closed-Circular Duplex DNA by Chromatography on Hydroxyapatite in the Presence of Ethidium Bromide".
Montbriand et al., J. Biotechnol. 44 (1996) 43-46, "Improved method for the removal of endotoxin from DNA".
Marquet et al., BioPharm (Sep. 1995) 26-37, "Process Development for the Manufacture of Plasmid DNA Vectors for use in Gene Therapy".
Genthner et al., *App. Environ. Microbiology*, 1985, vol. 50, pp. 1007-1013.
Response to Patentee's Comments in Relation to Novelty and Attached Declaration of Phillip Henwood submitted Sep. 30, 2005 in Opposition proceedings against corresponding EP08805367B.
Vincent et al., Analytical Biochemistry, vol. 110, 1981, pp. 123-127.
Chow, Nucleic Acids Research, vol. 17, No. 20, 1989, p. 8391.
Henninger et al., Biol. Chem. Hoppe-Seyler, vol. 374, 1993, pp. 625-634.
Yamagishi et al., Gene, vol. 26, 1983, pp. 317-321.
Verma et al., Nature, vol. 389, 1997, pp. 239-242.
Anderson, Nature, vol. 392-supplement, 1998, pp. 25-30.
Juengst, BMJ, vol. 326, 2003, pp. 1410-1411.
Stadler et al., The Journal of Gene Medicine, vol. 6, 2004, pp. S564-S66.
Quagen News 1/26, "Ultrapure Endotoxin-Free Plasmid Prep.", pp. 2-5, Issue No. 1, 1996.

PROCESS FOR PREPARING PURIFIED NUCLEIC ACID AND THE USE THEREOF

This application is a continuation of application Ser. No. 13/938,398 filed Jul. 10, 2013, which is a divisional of application Ser. No. 13/545,427, filed Jul. 10, 2012, which is a divisional of application Ser. No. 13/197,225 filed Aug. 3, 2011, which is a divisional of application Ser. No. 12/627,449 filed Nov. 30, 2009, which is a divisional of application Ser. No. 11/389,167 filed Mar. 27, 2006, which is a continuation of U.S. Ser. No. 10/771,371 filed Feb. 5, 2004, which is a divisional of U.S. Ser. No. 09/117,537 filed Aug. 4, 1998, now U.S. Pat. No. 6,750,333, which is a 35 USC 371 of PCT/EP97/00321 filed Jan. 24, 1997, which claims the benefit of EP96101628.4 filed Feb. 6, 1996, the disclosures of which are incorporated herein in their entirety by reference.

The invention concerns the preparation of purified nucleic acid and its use especially in gene therapy.

Replicatable nucleic acid is usually produced by amplifying replicatable plasmid DNA in gram-negative bacteria such as e.g. *E. coli*. After lysis of the biomass (usually alkaline lysis with lysozyme or ultrasound), it is centrifuged and the supernatant is shaken out with phenol. Subsequently an ultracentrifugation on a caesium chloride gradient is carried out (Birnboim & Doly, Nucleic Acid Res. 7 (1979) 1513-1523, Garger et al., Biochem. Biophys. Res. Comm. 117 (1983) 835-842). However, such preparations contain endotoxins, phenol, caesium chloride and/or ethidium bromide as a dye.

A further process is described in the QIAGEN® Plasmid Handbook (Qiagen Inc., Chatsworth, USA) and EPS-B 0 268 946. According to this process the cell lysate obtained after a conventional lysis is chromatographed on QIAGEN®-TIP, which contains QIAGEN® resin (a support material based on silica). The disadvantage of this process is that DNA binding proteins are not completely detached from the DNA and therefore the purified plasmid fraction contains proteins and in particular endotoxins (from the membrane of the gram-negative host cells) in considerable amounts.

In another process after alkaline lysis of the *E. coli* biomass the centrifugation supernatant is chromatographed according to Birnboim & Doly under high salt conditions over anion exchange columns (e.g. Mono-Q, Source-Q from Pharmacia, Macroprep-Q from BioRad, Poros-Q from Perseptive Biosystems or HyperD-Q from Biosepra, cf. Chandra et. al., Analyt. Biochem. 203 (1992) 169-172; Dion et al., J. Chrom. 535 (1990) 127-147). Also in this case the purified plasmid fraction contains proteins and in particular endotoxins in considerable amounts.

In another process after alkaline lysis and subsequent Phenol/chloroform extraction it is possible to chromatograph by gel filtration (McClung & Gonzales, Analyt. Biochem. 177 (1989) 378-382; Raymond et al., Analyt. Biochem. 173 (1988) 125-133). Even after this purification the plasmid preparation contains impurities and in particular phenol.

A process for the isolation and purification of nucleic acids for use in gene therapy is described in WO 95/21177 in which the purification is essentially carried out by centrifugation, filtration, affinity chromatography or chromatography on an inorganic chromatographic material with subsequent chromatography on an ion exchanger. An additional removal of endotoxins can then be achieved according to WO 95/21177 when the nucleic acid is treated with an endotoxin removal buffer which contains 10% Triton®X100 and 40 mmol/l MOPS buffer (3-morpholino-1-propanesulfonate buffer). A disadvantage of this process is that the nucleic acid purified in this manner contains impurities of Triton® and MOPS buffer. Although endotoxins can be removed by this process to a content of ca. 100 EU/mg DNA (Qiagen News 1/96, 3-5), it is not possible to remove endotoxins to a greater extent by this process.

However, for a therapeutic application such as for example for gene therapy a nucleic acid preparation is required which is as free as possible of all impurities (in particular substantially free of endotoxins). Above all the endotoxin content of plasmid preparations has been hitherto an unsolved problem as described for example by Cotten et al., Gene Therapy 1 (1994) 239-246. A reduced endotoxin content (ca. 100 EU/mg DNA) can only be achieved by the state of the art such as for example according to WO 95/21177 if the nucleic acids are treated with non-ionic detergents such as e.g. Triton (endotoxin removal buffer from WO 95/21177). However, Triton® has a biological action such as e.g. lung changes or reduction of blood pressure (Fiedler, "Lexikon der Hilfstoffe für Pharmazie und Kosmetik und angrenzende Gebiete (Band 9, 3rd edition, 1989, Editio Cantor, DE)). The MOPS buffer which is additionally required also contains a substance that is problematic with regard to a therapeutic application.

The invention provides a nucleic acid preparation, preferably a plasmid DNA, of high purity in which endotoxins are substantially removed and preferably without ethidium bromide, phenol, caesium chloride, polymyxin or non-ionic detergents and also provides a simple and effective process for purifying such nucleic acids in particular for removing endotoxins.

The invention concerns a nucleic acid that can be replicated in gram-negative bacteria, preferably a plasmid DNA with a content of less than 1% protein, preferably less than 0.1% protein and a content of less than 1 EU/mg DNA, preferably 0.01-0.1 EU/mg DNA of endotoxins. This plasmid DNA is preferably free of ethidium bromide, phenol and caesium chloride, free of detergents based on octylphenol-poly(ethylene glycol ether)$_n$ such as Triton® detergents and also free of MOPS buffer substance and RNAse.

Amplification is understood as an increase in the copy number of a nucleic acid (in particular DNA and plasmid DNA) based on the replication of a vector. In this process numerous copies are produced from a template. A vector is replicated which represents the nucleic acid or which contains the cloned nucleic acid.

A plasmid DNA is understood as an extrachromosomal DNA duplex molecule. The size of a DNA plasmid is usually 1 to more than 200 kb and one to several hundred copies are present in host cells. Plasmid DNA is usually amplified in gram-negative bacteria such as e.g. *E. coli* and subsequently isolated. Plasmids are often used to construct cloning vectors, for the transfection of prokaryotic and eukaryotic cells. A therapeutic use is of especial importance in connection with in vivo and ex vivo gene therapy. Plasmid DNA that is used therapeutically preferably has a length of 5 to 20 kb, particularly preferably 5-10 kb and is double-stranded. The plasmid DNA can be linearized or circularly closed. Preferably DNA is used that is essentially circularly closed.

Consequently the invention additionally concerns a pharmaceutical composition containing a nucleic acid according to the invention, preferably plasmid DNA, in a therapeutically effective amount and optionally additional pharmaceutical auxiliary substances, fillers or additives.

Endotoxins are lipopolysaccharides from gram-negative bacteria. Endotoxins can have a pyrogenic effect in mammals and induce an endotoxin shock. The main toxic component of endotoxins is lipid A, the polysaccharide moiety mediating the water solubility and the lipid moiety having the toxic effect. The biological effect of endotoxins in mammals are in particular a hypersensitization as well as other reactions which are accompanied by fever.

Plasmid DNA is amplified by standard methods in *E. coli* i.e. a gram-negative bacterium. After fermentation the biomass obtained in this process is lysed and the cells are lysed. In this process the endotoxins are released from the cell membrane. This means that after amplification of nucleic acids, in particular of plasmid DNA, in gram-negative bacteria and in particular in *E. coli* it is necessary to remove endotoxins if it is intended to use this plasmid DNA therapeutically.

Depending on the application doses of 50 µg to 10 mg and more are used or planned or a therapeutic application of replicatable nucleic acids, in particular of plasmid DNA. The dose amount depends on the disease and type of administration. In an aerosol, e.g. for the treatment of cystic fibrosis, doses of 400 µg and more are used. This applies likewise to plasmid DNA encapsulated in a lipid complex (e.g. in liposomes). In order to provide such amounts of replicatable nucleic acid that can be used therapeutically, it is necessary to produce the replicatable nucleic acid on a large scale. For this fermentation preparations are expedient with 1-5 kg biomass from which 1-5 g nucleic acid can be isolated.

The invention also concerns a process for the production of a plasmid DNA with a content of less than 1 EU/mg DNA, preferably 0.01-0.1 EU/mg DNA of endotoxins which is characterized in that plasmid DNA is replicated in gram-negative bacteria, the biomass is lysed and the soluble components are chromatographed on hydroxylapatite and subsequently the said plasmid DNA is isolated. Before chromatography on hydroxylapatite it is preferably to carry out an ion exchange chromatography which essentially removes RNA and foreign proteins. This can optionally remove further impurities and achieve a content of nucleic acid of less than 1% protein, preferably less than 0.1% protein, free of ethidium bromide, phenol and caesium chloride. Such a preparation is also preferably free of detergents based on octylphenol poly(ethylene glycol ether)$_n$ and MOPS buffer substance.

The process according to the invention enables numerous impurities to be avoided or removed which plasmid DNA contains if it is produced by a process familiar to a person skilled in the art. Above all it is surprisingly possible to drastically reduce the endotoxin content in a simple manner.

In the process according to the invention an outstanding removal of endotoxins is achieved by the chromatography with hydroxylapatite. This is all the more surprising since chromatography on hydroxylapatite is only used in the literature to separate DNA and RNA (Johnson & Ilan, Analyt. Biochem. 132 (1983) 20-25).

The chromatographic effect of hydroxylapatite is essentially based on the interaction between calcium$^{2+}$ groups and the negative charge of the nucleic acid to be purified and to a lesser extent on the interaction of the nucleic acid to be purified with $PO_4^{3-}$ groups on the surface of crystalline hydroxylapatite (cf e.g. Protein Purification Methods, Ed. by Elv. Harries and S. Angal, Oxford University Press 1989, 238-244). Chromatography on hydroxylapatite can be essentially referred to as an ion exchanger step for nucleic acids in which the bound DNA cannot be eluted from the hydroxylapatite matrix by a simple increase of ionic strength (e.g. NaCl) but rather by increasing the concentration, preferably of phosphate or citrate, divalent metal ions and/or EDTA.

In the process according to the invention endotoxins and the nucleic acid to be purified are firstly bound to hydroxylapatite primarily via dipole-dipole interactions in the chromatography on hydroxylapatite (e.g. HA-ceramic, BioGel HPHT, Bio-Gel HT/HTP from Biorad DE, HA-Ultrogel from IBF or HA spheroidal from BDH, Macrosorb C from Sterling Organics). The equilibration is usually carried out at neutral pH in phosphate buffer. A denaturing agent is preferably added, as in the subsequent washing of the column. Surprisingly it is possible to displace the nucleic acid from its binding to hydroxylapatite with phosphate, citrate or calcium ions whereas the endotoxins remain bound. Instead of calcium, the displacement of the nucleic acid from its binding to hydroxylapatite can be achieved with other divalent metal ions which can replace calcium in the apatite such as e.g. Mg, Fe, Mn. For the elution the ion concentration is preferably 100 mmol/l or more. Ion concentrations between 100 and 500 mmol/l or 200 and 500 mmol/l are particularly preferred. A solution containing phosphate ions (e.g. phosphate buffer) is particularly preferably used. Before the elution (without denaturing agent) it is expedient to wash (with denaturing agent). It has turned out to be advantageous to for example use a phosphate of sulfate solution (100-200 mmol/l) to which a denaturing agent (e.g. urea or guanidine hydrochloride) has been added at a DNA-denaturing concentration (e.g. 6 mol/l urea).

In a preferred embodiment an ultrafiltration is additionally carried out after the chromatography on hydroxylapatite.

In order to produce the nucleic acid according to the invention the plasmids which represent or contain the nucleic acid are usually amplified in gram-negative bacterial cultures. Such methods are known to a person skilled in the art and are described for example by Sambrook et al. (1989), Molecular Cloning: A Laboratory Manual, 2nd edition, Cold Spring Harbor Laboratory Press and by F. M. Ausubel et al., eds. (1991), Current Protocols in Molecular Biology, Wiley Interscience, New York. For this the bacterial cultures which contain the plasmids are firstly subcultured and subsequently cultured in a suitable medium optionally with addition of a selection agent.

The biomass is also lysed by methods familiar to a person skilled in the art (mechanical or enzymatic lysis, see e.g. Birnboim and Doly, Nucleic Acids Research 7 (1979) 1513-1423) without addition of RNAse. It is possible to omit shaking out with phenol if the proteins are separated by chromatography on an anion exchanger. After lysis and separation of the insoluble components, preferably by centrifugation and filtration over a filter candle (5 µm pores), the cell supernatant is preferably firstly chromatographed on an anion exchanger to remove proteins. Suitable anion exchangers are anion exchangers based on agarose such as for example Q-Sepharose. Other suitable anion exchangers are based on polymethacrylate (Macroprep/Bio-Rad, Germany), polystyrene/divinylbenzene (Poros/Perseptive, HyperD/Biosepra, Source/Pharmacia) or silica gel on the surface of which diethylaminoethyl (DEAE) or dimethylaminoethyl (DMAE) groups are for example bound.

In order to optimize the purification effect, the nucleic acid is eluted by means of a high salt gradient e.g. NaCl gradient (preferably 0.65 mol/l-0.85 mol/l) in TE buffer. This surprisingly enables numerous impurities (RNA, protein) to be separated in one step.

It is also preferable to carry out an additional Isopropanol/ethanol precipitation, preferably after the hydroxylapatite chromatography, to minimize the bioburden and for desalting. Subsequently the nucleic acid according to the invention can be bottled under sterile conditions.

The following examples describe the invention in more detail.

EXAMPLE 1

Isolation of Nucleic Acid from E. Coli Biomass

E. coli biomass containing plasmid DNA is lysed by an alkaline lysis and the released plasmid DNA is chromatographed over Q-Sepharose and HA-Ceramic. The eluate is desalted by an isopropanol/ethanol precipitation and concentrated and the plasmid DNA precipitate is resuspended in TE buffer.

Resuspension buffer: 50 mmol/l Tris/HCl, 10 mmol/l EDTA-$Na_2$, pH 8.0±0.2

Potassium acetate buffer: 3 mol/l potassium acetate buffer pH 5.5

60 g biomass (wet, E. coli) from the fermenter is filled into depyrogenized centrifuge beakers. 750 ml resuspension buffer is added and it is stirred slowly (ca. 35 rpm) for at least 24 hours at 5±4° C. until the biomass is completely suspended. During this process the temperature of the suspension is slowly increased to 25° C.

750 ml 0.2 mol/l NaOH/1% SDS is added to the suspension while stirring at ca 80 rpm and incubated for 5 minutes at 25° C. 750 ml potassium acetate buffer (see above) is added while stirring and the temperature of the biomass is lowered as rapidly as possible to 4° C.

The biomass is centrifuged for 30 minutes at 26000×g and 4° C. The supernatant which contains the plasmid DNA is decanted and filtered clear over a 5 µm filter candle.
Chromatography on Q-Sepharose ff:

TE buffer: 10 mmol/l Tris-HCl, 1 mmol/l EDTA pH 8.0±0.2

Equilibration/wash buffer=gradient buffer A: 10 mmol/l Tris-HCl, 1 mmol/l EDTA, 0.65 mol/l NaCl pH 8.0±2.

Gradient buffer B: 10 mmol/l Tris-HCl, 1 mmol/l EDTA, 0.85 mol/l NaCl pH 8.0±0.2.

The decanted centrifuge supernatant is adjusted to 49-50 mS/cm conductivity by addition of ca. 350 ml TE buffer/l centrifugation supernatant and cooled to 5°±4° C. The whole chromatography is carried out at this temperature. The centrifugation supernatant is applied to the equilibrated column at 5-8 column volumes (CV)/h. Subsequently the column is washed at a flow rate of 5-8 CV/h with ca. 8 CV 10 mmol/l Tris-HCl, 1 mmol/l EDTA, 0.65 mol/l NaCl pH 8.0±0.2.

Elution

A gradient is applied to the column (5 CV buffer A, 5 CV buffer B) and the eluate is fractionated at a flow rate of 5-8 CV/h. The detection is carried out at 254 nm. The pre-peak (impurities) is separated from the main peak (plasmid DNA) by collecting the main peak from the increasing flank onwards in a separate vessel. The endotoxin content of the eluate is between 1200 and 12000 EU/mg plasmid DNA.
Chromatography on Hydroxylapatite (HA Ceramic)

The chromatography is carried out at 5±4° C.
Equilibration buffer: 0.1 mol/l potassium phosphate, 6 mol/l urea pH 7.0±0.2
wash buffer 1: 0.15 mol/l potassium phosphate, 6 mol/l urea pH 7.0±0.2
wash buffer 2: 0.02 mol/l potassium phosphate buffer pH 7.0±0.2
elution buffer: 0.5 mol/l potassium phosphate pH 7.0±0.2

The detection is carried out at 254 nm with a UV detector/plotter unit. A 1% product solution (plasmid DNA) measured with a calibrated photometer is used as a calibration solution.

The Q-Sepharose® pool is adjusted to a final concentration of 1.1 mmol/l calcium chloride and applied to the equilibrated column at a flow rate of 5-8 CV/h.

Subsequently the column is consecutively washed at a flow rate of 5-8 CV/h with:
1. 0.1 mol/l potassium phosphate, 6 mol/l urea pH 7.0±0.2, until absorbance is no longer detectable on the detector.
2. 2-4 CV, 0.15 mol/l potassium phosphate, 6 mol/l urea pH 7.0±0.2
3. 5 CV, 0.02 mol/l potassium phosphate pH 7.0±0.2

Following the wash steps it is eluted with 0.5 mol/l potassium phosphate buffer pH 7.0±0.1 at a flow rate of 5-6 CV/h.

The peak is collected, heated to 25° C. and 10% of it's volume of 4 mol/l KCl solution is added. Subsequently 0.7 parts by volume (relative to the volume of the eluate) of isopropanol is added, the solutions are mixed and incubated for 5-10 minutes at 25° C. It is centrifuged for 30 minutes at ≥20,000×g, the plasmid DNA being in the precipitate.

20 ml 70% ethanol is added to the precipitate and it is again centrifuged for 10-15 minutes at ≥20,000×g at 4° C.

The precipitate which contains the plasmid DNA is resuspended in TE buffer (10 mmol/l Tris-HCl, 1 mmol/l EDTA pH 8.0+0.2) and adjusted to a plasmid concentration of 1 mg/ml. The endotoxin content is typically less than 0.06 EU/mg DNA and between 0.01 and 0.06 EU/mg DNA.

The endotoxin content is determined by adding a limulus amoebocyte lysate solution (LAL solution) to the solution to be examined. Endotoxins result in a gel formation in this mixture.

No gel formation should occur in the negative control preparations and in the positive control preparations as well as in the sample solutions supplemented with two λ control standard endotoxin a gel formation must occur.

The first dilution step of the solution of active substance for which these criteria apply and in which no gel formation occurs is used to calculate the endotoxin content of the solution of active substance solution according to the following formula:

$$E = V \times \lambda \text{ (EE/ml)}$$

E: endotoxin content
V: dilution factor
λ: lysate sensitivity (EE/ml)

EXAMPLE 2

Plasmid Preparation According to the State of the Art

The plasmid preparation is carried out analogously to Birnboim et al., Nucl. Acids Res. 7 (1979) 1513-1523 and Meth. Enzymol. 100 (1983) 243-255. Accordingly the bacterial cells are lysed in NaOH/SDS in the presence of RNase. It is centrifuged and the supernatant which contains the plasmid DNA is processed further. The supernatant is loaded onto a pre-equilibrated Qiagen® column.

The bacterial mass is resuspended in 4 ml buffer (100 µg/ml RNase A, 50 mmol/l TriS-HCl, 10 mmol/l EDTA, pH 8.0). 4 ml lysis buffer (200 mmol/l NaOH, 1% SDS) is added and it is incubated for 5 minutes at room temperature. Subsequently 4 ml neutralisation buffer (3 mol/l potassium acetate, pH 5.5) is added and it is incubated for 15 minutes at 4° C. It is centrifuged for 30 minutes at 30,000×g at the same temperature and the supernatant is processed further. A Qiagen® column is equilibrated with 4 ml equilibration buffer (750 mmol/l NaCl, 50 mmol/l MOPS, 15% ethanol, pH 7.0, 0.15% Triton®X 100) and the supernatant is applied to the column. It is washed with 1 mol/l NaCl, 50 mmol/l MOPS, 15% ethanol, pH 7.0 and eluted with 5 ml elution buffer (1.25 mol/l NaCl, 50 mmol/l Tris-HCl, 15% ethanol, pH 8.5).

The eluate is precipitated with isopropanol (0.7 vol) and centrifuged for 30 minutes at 15,000×g at 4° C. The DNA pellet is washed in 70% ethanol and again centrifuged. Subsequently the pellet is resolubilized in 10 mmol/l Tris-HCl, 1 mmol/l EDTA, pH 8.0.

The endotoxin content of such a plasmid preparation is typically 300-3000 EU/mg. Using an endotoxin removal buffer according to WO 95/21177 and Qiagen news 1/96, p. 3-5 the endotoxin content can be further reduced to ca. 100 EU/mg.

LIST OF REFERENCES

Ausubel, F. M., et al. eds. (1991), Current Protocols in Molecular Biology, Wiley Interscience, New York
Birnboim, H. C. and Doly, J., Nucleic Acids Research 7 (1979) 1513-1523
Birnboim, H. C., et al., Meth. Enzymol. 100 (1983) 243-255
Chandra et al., Analyt. Biochem. 203 (1992) 169-172
Cotten et al., Gene Therapy 1 (1994) 239-246
Dion et al., J. Chrom. 535 (1990) 127-147
European Patent EP-B 0 268 946
Fiedler, Lexikon der Hilfsstoffe für Pharmazie und Kosmetik und angrenzende Gebiete (Vol. 9, 3rd edition, 1989, Editio Cantor, GER)
Garger et al., Biochem. Biophys. Res. Comm. 117 (1983) 835-842
Johnson & Ilan, Analyt. Biochem. 132 (1983) 20-25
McClung & Gonzales, Analyt. Biochem. 177 (1989) 378-382
Protein Purification Methods, Ed. by Elv. Harries and S. Angal, Oxford University Press 1989, 238-244
QIAGEN NEWS 1/96, 3-5
QIAGEN Plasmid Handbook (Qiagen Inc., Chatsworth, USA)
Raymond et al., Analyt. Biochem. 172 (1988) 125-133
Sambrook, J. et al. (1989), Molecular Cloning: A Laboratory Manual, 2nd edition, Cold Spring Harbor Laboratory Press, New York, USA
WO 95/21177

The invention claimed is:
1. A process for making a DNA preparation, comprising:
(a) providing gram-negative bacteria containing said DNA and replicating said DNA in said gram-negative bacteria;
(b) lysing said bacteria to obtain a lysate, wherein the lysate is a DNA-containing fraction;
(c) filtering the lysate to obtain a filtrate and fractionating said filtrate by gel filtration;
(d) chromatographing any DNA-containing fraction on an anion exchanger; and thereafter;
(e) chromatographing said DNA-containing fraction on hydroxylapatite,
(f) eluting said hydroxylapatite in step (e) with a solution of phosphate, citrate, sulfate or divalent metal ions in order to obtain said DNA preparation, wherein said DNA preparation comprises a bacterially produced DNA, has proteins in an amount of less than about 0.1% DNA, and endotoxins in an amount of less than about 1 EU/mg DNA; wherein the DNA preparation is free of ethidium bromide, phenol, cesium chloride, octylphenolpoly(ethylene glycol ether)$_n$, detergents and MOPS buffer.

* * * * *